(12) United States Patent
Devore et al.

(10) Patent No.: US 11,235,089 B2
(45) Date of Patent: Feb. 1, 2022

(54) INJECTABLE IN SITU POLYMERIZABLE COLLAGEN COMPOSITION

(71) Applicants: SHANGHAI HAOHAI BIOLOGICAL TECHNOLOGY CO., LTD., Shanghai (CN); SHANGHAI QISHENG BIOLOGICAL PREPARATION CO., LTD., Shanghai (CN)

(72) Inventors: Dale P. Devore, Chelmsford, MA (US); Robert J. Brooks, Columbia, MO (US); Todd Byrne, Columbia, MO (US)

(73) Assignees: Shanghai Haohai Biological Technology Co., Ltd., Shanghai (CN); Shanghai Qisheng Biological Preparation Co., Ltd., Shanghai (CN)

( * ) Notice: Subject to any disclaimer, the term of this patent is extended or adjusted under 35 U.S.C. 154(b) by 0 days.

(21) Appl. No.: 16/164,052

(22) Filed: Oct. 18, 2018

(65) Prior Publication Data
US 2019/0046686 A1 Feb. 14, 2019

Related U.S. Application Data

(63) Continuation of application No. 14/430,741, filed as application No. PCT/US2014/020217 on Mar. 4, 2014, now Pat. No. 10,111,981.

(60) Provisional application No. 61/851,119, filed on Mar. 4, 2013.

(51) Int. Cl.
| | |
|---|---|
| *A61L 27/24* | (2006.01) |
| *A61K 8/34* | (2006.01) |
| *A61Q 19/08* | (2006.01) |
| *A61K 8/65* | (2006.01) |
| *A61K 8/60* | (2006.01) |
| *A61L 27/34* | (2006.01) |
| *A61L 27/50* | (2006.01) |
| *A61L 27/54* | (2006.01) |

(52) U.S. Cl.
CPC ............ *A61L 27/24* (2013.01); *A61K 8/345* (2013.01); *A61K 8/60* (2013.01); *A61K 8/65* (2013.01); *A61L 27/34* (2013.01); *A61L 27/505* (2013.01); *A61L 27/54* (2013.01); *A61Q 19/08* (2013.01); *A61K 2800/95* (2013.01); *A61L 2300/412* (2013.01); *A61L 2400/06* (2013.01); *A61L 2430/34* (2013.01)

(58) Field of Classification Search
CPC ............ A61L 27/34; A61L 2300/412; A61L 2400/06; A61L 2430/34; A61L 27/24; A61L 27/505; A61L 27/54; C08L 89/06; A61K 2800/95; A61K 8/345; A61K 8/65; A61K 8/60; A61Q 19/08
See application file for complete search history.

(56) References Cited

U.S. PATENT DOCUMENTS

| | | | |
|---|---|---|---|
| 3,949,073 | A | 4/1976 | Daniels et al. |
| 4,424,208 | A | 1/1984 | Wallace et al. |
| 4,488,911 | A | 12/1984 | Luck et al. |
| 4,582,640 | A | 4/1986 | Smestad et al. |
| 4,592,864 | A | 6/1986 | Miyata et al. |
| 4,642,117 | A | 2/1987 | Nguyen et al. |
| 4,803,075 | A | 2/1989 | Wallace et al. |
| 4,969,912 | A * | 11/1990 | Kelman .................. A61L 27/24 128/898 |
| 4,992,226 | A | 2/1991 | Piez et al. |
| 5,037,377 | A | 8/1991 | Alonso |
| 5,162,430 | A | 11/1992 | Rhee et al. |
| 5,292,802 | A | 3/1994 | Rhee et al. |
| 5,306,500 | A | 4/1994 | Rhee et al. |
| 5,324,775 | A | 6/1994 | Rhee et al. |
| 5,328,955 | A | 7/1994 | Rhee et al. |
| 5,376,375 | A | 12/1994 | Rhee et al. |
| 5,413,791 | A | 5/1995 | Rhee et al. |
| 5,428,024 | A | 6/1995 | Chu et al. |
| 5,436,135 | A | 7/1995 | Tayot et al. |
| 5,446,091 | A | 8/1995 | Rhee et al. |
| 5,475,052 | A | 12/1995 | Rhee et al. |
| 5,476,515 | A | 12/1995 | Kelman et al. |
| 5,492,135 | A | 2/1996 | DeVore et al. |
| 5,510,418 | A | 4/1996 | Rhee et al. |
| 5,550,188 | A | 8/1996 | Rhee et al. |

(Continued)

FOREIGN PATENT DOCUMENTS

| | | |
|---|---|---|
| EP | 2033689 | 3/2009 |
| EP | 2042201 B1 | 8/2011 |

(Continued)

OTHER PUBLICATIONS

DeVore et al., "In situ Polymerizing Collagen Gel for Sealing Corneal Incisions and Scleral Injection Tunnels", Abstract 3582 (2012) (1 pg). (Year: 2012).*

(Continued)

*Primary Examiner* — Michael B. Pallay
(74) *Attorney, Agent, or Firm* — Stinson LLP (57) ABSTRACT

The present invention is directed to injectable acid soluble collagen compositions comprising a neutralized solution of an acid soluble collagen, EDTA and preferably a polyol, wherein the composition is injectable at physiological pH and the acid soluble collagen polymerizes upon exposure to tissue. The invention is suitable for use in soft tissue augmentation, promoting soft tissue regeneration and coating medical implants and devices.

16 Claims, 3 Drawing Sheets

(56) References Cited

U.S. PATENT DOCUMENTS

| | | | |
|---|---|---|---|
| 5,699,810 A * | 12/1997 | Pallikaris | A61F 9/013 128/898 |
| 5,800,541 A | 9/1998 | Rhee et al. | |
| 5,807,581 A | 9/1998 | Rosenblatt et al. | |
| 5,823,671 A | 10/1998 | Mitchell et al. | |
| 5,861,486 A | 1/1999 | DeVore et al. | |
| 6,051,648 A | 4/2000 | Rhee et al. | |
| 6,096,309 A | 8/2000 | Prior et al. | |
| 6,204,365 B1 | 3/2001 | DeVore et al. | |
| 6,509,031 B1 | 1/2003 | Miller et al. | |
| 6,682,760 B2 | 1/2004 | Noff et al. | |
| 6,833,408 B2 | 12/2004 | Sehl et al. | |
| 7,025,916 B2 | 4/2006 | Bachrach | |
| 7,064,187 B2 | 6/2006 | Stone | |
| 7,244,270 B2 | 7/2007 | Lesh | |
| 7,412,978 B1 | 8/2008 | Keller | |
| 7,595,377 B2 | 9/2009 | Stone | |
| 7,964,704 B2 | 6/2011 | Huang | |
| 8,067,031 B2 | 11/2011 | Daniloff et al. | |
| 8,084,055 B2 | 12/2011 | Voytik-Harbin et al. | |
| 2001/0055615 A1 | 12/2001 | Wallace et al. | |
| 2002/0068089 A1 | 6/2002 | Vogel et al. | |
| 2003/0181371 A1 | 9/2003 | Hunter et al. | |
| 2004/0234574 A9 | 11/2004 | Sawhaney et al. | |
| 2005/0069573 A1 | 3/2005 | Cohn et al. | |
| 2005/0175665 A1 | 8/2005 | Hunter et al. | |
| 2005/0281883 A1 | 12/2005 | Daniloff et al. | |
| 2006/0095016 A1 | 5/2006 | Pauza et al. | |
| 2006/0100138 A1 | 5/2006 | Olsen et al. | |
| 2007/0003525 A1 | 1/2007 | Moehlenbruck et al. | |
| 2007/0020225 A1 * | 1/2007 | Abramson | C08H 1/06 424/78.27 |
| 2007/0065484 A1 | 3/2007 | Chudzik et al. | |
| 2007/0196454 A1 | 8/2007 | Stockman et al. | |
| 2008/0003619 A1 * | 1/2008 | Lutz | C12N 9/20 435/7.4 |
| 2009/0117070 A1 | 5/2009 | Daniloff et al. | |
| 2009/0117188 A1 | 5/2009 | Gershkovich et al. | |
| 2009/0215923 A1 | 8/2009 | Carnahan et al. | |
| 2010/0159011 A1 | 6/2010 | Lian et al. | |
| 2010/0215715 A1 | 8/2010 | Han et al. | |
| 2011/0104052 A1 | 5/2011 | Barnett et al. | |
| 2013/0052155 A1 | 2/2013 | Marcolongo et al. | |
| 2013/0096064 A1 * | 4/2013 | Chandler | A61K 45/06 514/17.2 |
| 2013/0129807 A1 | 5/2013 | DeVore et al. | |
| 2014/0193473 A1 * | 7/2014 | Yoder | A61L 27/24 424/422 |

FOREIGN PATENT DOCUMENTS

| | | |
|---|---|---|
| WO | WO 1993/002639 | 2/1993 |
| WO | WO 2000/47114 | 8/2000 |
| WO | WO 2000/47130 | 8/2000 |
| WO | WO 2002/40072 | 5/2002 |
| WO | WO 2004/073759 | 9/2004 |

OTHER PUBLICATIONS

Hayashi et al., "Factors Affecting the Interactions of Collagen Molecules as Observed by in vitro Fibril Formation", 1972, J. Biochem., vol. 72, pp. 749-758. (Year: 1972).*

"Augment." The Merriam-Webster.com Dictionary, Merriam-Webster Inc., https://www.merriam-webster.com/dictionary/augment. Accessed Jan. 14, 2020. (Year: 2020).*

Written Opinion issued for corresponding PCT/US2014/020217 dated Jul. 10, 2014 (4 pgs).

Corrected International Search Report and Written Opinion issued for corresponding PCT/US2014/020217 dated Dec. 7, 2015 (15 pgs).

Smith et al., "Novel Activity Assays for the Collagenases MMP-1 and MMP-13", 10th National Converence, Sep. 24-28, 2000, Virginia (1 pg).

Boland, "Effects of D-glucose, L-glucose and D-mannitol on renal calcium handling and general renal function in the rat", Experimental Physiology, 1993, 78, pp. 165-174 (10 pgs).

DeVore et al., "In Situ Polymerizing, Collagen-based Drug Delivery Vehicle", Abstract 5126 (2006) (3 pgs).

DeVore et al., "In situ Polymerizing Collagen Gel for Sealing Corneal Incisions and Scleral Injection Tunnels", Abstract 3582 (2012) (1 pg).

DeVore, et al., "Sustained Delivery of Latanoprost from Collagen-Based Depots", Abstract 3241 (2011) (1 pg).

Jimenez Hamann et al., "Novel intrathecal delivery system for treatment of spinal cord injury", Experimental Neurology 182 (2003) pp. 300-309 (10 pgs).

DeVore, et al., "Collagen Fibril Formation at Microgravity Conditions: Fibrillogenesis under Diffusion Control", Abstract (2001) (1 pg).

Denton, et al., Chapter 13—"Review of Collagen Fillers" in Office-based Cosmetic Procedures and Techniques, Cambridge University Press (2010) pp. 59-64 (6 pgs).

Baumann et al., Chapter 23—"Dermal Fillers", in Cosmetic Dermatology-Principles and Practice, McGraw Hill (2009) pp. 191-211 (21 pgs).

Root et al., "Inhibitory Effect of Disodium EDTA upon Growth of *Staphylococcus epidermidis* in Vitro: Relation to Infection Prophylaxis of Hickman Catheters", Antimicrobial Agents and Chemotherapy, vol. 32 (1988) pp. 1627-1631 (5 pgs).

Woolley et al., "Purification, Characterization and Inhibition of Human Skin Collagenase", Biochem. J. vol. 169 (1978) pp. 265-276 (14 pgs).

DeVore, "Tissue Augmentation: Past, Present, and Future Filler Compositions", Presentation given at Technological Innovations in Plastic Surgery (2011) (33 pgs).

Guo, et al., "The Effect of Low concentration of EDA on Biofilm Formation of *Staphylococcus aureus*", Food and Fermentation Industries, Vo. 38, No. 12, Dec. 31, 2012 (in Chinese with only the Abstract and Paragraph 2.3 of the article in English).

DeVore et al., "Journal of Biomedical Materials Research", 104: 758-767 (2016).

Hayashi et al., J. Biochem, 72: 749-758 (1972).

* cited by examiner

INJECTABLE IN SITU POLYMERIZABLE COLLAGEN COMPOSITION

CROSS-REFERENCE TO RELATED APPLICATIONS

This application claims priority to and is a Continuation of U.S. patent application Ser. No. 14/430,741, filed on Mar. 4, 2014, which is a U.S. National Stage of International Application Number PCT/US2014/020217 filed on Mar. 4, 2014, which published on Sep. 12, 2014 under International Publication Number WO 2014/138021, which is based on and claims priority to U.S. Provisional Application Ser. No. 61/851,119 filed on Mar. 4, 2013, each of which is incorporated herein by reference in its entirety.

STATEMENT REGARDING FEDERALLY SPONSORED RESEARCH OR DEVELOPMENT

Not applicable.

STATEMENT REGARDING JOINT RESEARCH AGREEMENT

Not applicable.

BACKGROUND OF THE INVENTION

1. Field of the Invention

The present invention is directed to the field of collagen compositions and their methods of use.

2. Description of Related Art

Collagen compositions have been utilized for more than 30 years to augment or smooth out soft tissue defects such as dermal wrinkles and dermal folds, to volumize furrows, or to correct dermal contour unevenness and laxity.

The collagen compositions utilized for soft tissue augmentation have been comprised of either reconstituted collagen fibrils prepared from solubilized collagen extracted from animal hides, reconstituted collagen fibrils prepared from soluble recombinant human collagen or intact collagen fibrils or fibers processed from human skin. In all cases the collagen composition has been composed of collagen fibrils/fibers or crosslinked collagen fibrils/fibers.

Since soft tissues are primarily composed of collagen-based matrices, it makes sense to correct soft tissue defects with collagens or collagen-based compositions. There have been at least twelve FDA approved collagen products available for soft tissue augmentation in the U.S. since 1981. These products are generally called dermal fillers. However, at this time, most of the collagen-based fillers are no longer available in the U.S. market. They have been replaced by compositions that provide more durability including hyaluronic acid products, and products containing hydroxylapatite microbeads, poly-L-lactic acid particles, and polymethylmethacrylate microspheres.

There is still interest in having improved collagen-based compositions available for soft tissue augmentation. However, the compositions must exhibit increased durability.

BRIEF SUMMARY OF THE INVENTION

In certain embodiments, the invention is directed to an injectable acid soluble collagen composition comprising, a neutralized solution comprising the acid soluble collagen, EDTA and a polyol, wherein the composition is injectable at neutralized pH, and the acid soluble collagen polymerizes upon exposure to ion-containing fluids.

In certain embodiments, the invention is directed to a method for augmenting soft tissue, comprising injecting into a soft tissue deficiency an acid soluble collagen composition comprising, a neutralized solution comprising the acid soluble collagen and EDTA, wherein the composition is injectable at neutralized pH and wherein the acid soluble collagen polymerizes upon exposure to the tissue. In certain embodiments of the invention, the injected composition produces regeneration of the tissue.

In certain embodiments, the invention is directed to biocompatible medical implant, wherein the implant is comprised of a polymer or metal, and a coating of a neutralized acid soluble collagen composition covering at least a portion of the implant, wherein the collagen composition is solidified on the surface of the implant.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention relates to a unique collagen composition with applications for soft tissue augmentation and tissue regeneration, among other uses. The present invention is directed to injectable acid-soluble collagen compositions comprising a neutralized solution of an acid soluble collagen, EDTA and a polyol, wherein the composition is injectable at physiological pH and the acid-soluble collagen polymerizes upon exposure to tissue. In certain embodiments, the injectable, in situ polymerizable soluble collagen compositions are in the form of clear, injectable, viscous solutions at neutral pH. The compositions rapidly undergo polymerization involving initial gelation and subsequent fibrillization when contacted by or mixed with physiological fluids or other ion-containing fluids to form fibrous collagen matrices.

The collagen compositions are chemically treated with EDTA to produce temperature stable viscous solutions at neutral pH that exhibit anti-collagenase and anti-microbial characteristics. In addition, polyols, such as D-mannitol or other polyol osmolality enhancers, are preferably added to bring osmolality to physiological levels and to aid in stabilizing the soluble collagen composition during storage. The D-mannitol also improves biocompatibility. Sucrose, fructose, and other disaccharides may also be added to aid in stabilizing the composition during storage.

The compositions are suitable for use in soft tissue augmentation and promoting tissue regeneration. Anti-collagenase characteristics reduce or prevent digestion by tissue enzymes and anti-microbial characteristics provide additional assurance of sterility and prevention of biofilm formation. The compositions are also useful for coating medical implants.

The present invention further includes methods for augmenting soft tissue and tissue regeneration using in situ polymerizing collagen compositions of the present invention. The compositions are preferably in the form of a clear viscous, soluble, biocompatible collagen at neutral pH that can be easily injected through small needles (eg. 27 or 30 gauge) and upon injection into tissues rapidly undergo gelation and subsequent fibril formation. Upon interacting with tissue fluids, the composition nearly instantly forms a cohesive clear gel containing collagen molecular units that rapidly undergo fibril formation to form an opaque collagen matrix. In addition, the composition has been treated to include disodium EDTA in sufficient levels to impart anti-collagenase and bactericidal activity. It has been found that the in situ formed collagen matrix unexpectedly exhibits unique properties that prolong durability beyond that of known injectable collagen fillers. The EDTA imparts anti-collagenase activity by inhibiting tissue metalloproteinases that digest interstitial collagen and collagen matrices. It also imparts bactericidal activity to provide additional composition sterility and potentially inhibit biofilm formation.

The compositions of the present invention have shown durability and retained injection volume, with little or no reduction in original injection volume, for time periods of 4 weeks, 12 weeks and beyond 6 months. This property is different from most hyaluronic acid gels that increase in volume upon injection and then gradually lose volume over a period of months. In certain embodiments, upon injection into tissue, such as dermal tissue, the in situ polymerizing collagen composition forms a fibrous mass that integrates with surrounding tissue matrices.

Certain terms have the following meanings as use herein:

By "collagen" it is meant all types of collagen including those which have been processed or modified. The collagen may be of human or animal origin or may be produced using recombinant techniques. As used herein, collagen includes purified collagens as well as various collagen derivatives.

By "tissue" it is meant an aggregation of similarly specialized cells in an organism, preferably mammalian, and, most preferably human, where the cells are exposed to the organism's extracellular fluid.

By "in situ polymerization" it is meant formation of a cohesive collagen gel, and subsequently a collagen fibrillar mass, upon injection of the soluble collagen into tissue and not before injection.

By "gel mass" it is meant the clear gel that is formed immediately after the viscous collagen solution is injected into a physiologic solution or injected into tissue or exposed to ions that initiate polymerization. The clear gel mass becomes more opaque as it converts into a cohesive fibrillar collagen mass within minutes after making contact with physiologic fluids.

The collagen used to prepare the in situ polymerizing collagen may be extracted from animal hides, such as bovine hide or porcine hide, or may be cell derived human collagen, or recombinant human collagen. It is preferred that the base collagen be available in acid solution. Any acid soluble, fibril forming collagen type may be used. However, Types I and III collagen are preferred to prepare the in situ polymerizing collagen composition.

In one embodiment of the present invention, a neutralized, acid solubilized collagen, which remains in solution at physiological temperatures, is used in the in situ polymerizing collagen of the present invention. One method for initial treatment of the collagen to form such solution is disclosed in U.S. Pat. No. 5,492,135, which is incorporated herein by reference. In one embodiment, the soluble collagen may be isolated and purified from animal sources including bovine and porcine tissues or may be a recombinant human collagen. The resulting acidic collagen solution is preferably extensively dialyzed against disodium EDTA solutions to prevent premature collagen fibrillogenesis. During step-wise dialysis, the pH of the collagen solution is increased from acidic levels to a neutralized pH by adjusting the pH of the disodium EDTA dialysis solutions using 1N sodium hydroxide. The resulting neutralized pH is preferably between about 6.8 and about 7.5. At a neutralized pH, the collagen preparation does not undergo typical fibrillogenesis and remains clear and transparent until contacted by physiologic, or other ion-containing, fluids.

The collagen is present in the composition of the present invention in sufficient amounts to be injected through 27-31 gauge needles and cannula to provide effective tissue bulking, but not so concentrated that it cannot be injected through at least a 27 gauge needle or cannula or form a compact matrix that impermeable to host cells. In certain embodiments, the composition comprises the acid soluble collagen in a concentration between 5 and 70 mg/ml (0.5-7.0% w/v), between 25 and 65 mg/ml (2.5-6.5% w/v) or between 20 and 40 mg/ml (2-5% w/v).

The EDTA present in the composition is preferably disodium EDTA. The EDTA remaining in the injectable composition after dialysis is preferably present in sufficient concentration to provide anti-collagenase activity sufficient to inhibit activity of tissue metalloproteinases and to provide bactericidal activity to assure sterility and potentially inhibit biofilm formation. In certain embodiments, the concentration of the EDTA in the injectable composition is between 10 and 50 mM, between 25 mM and 40 mM, or between 30 mM and 35 mM.

In certain embodiments, the compositions of the present invention contain a polyol to bring the composition to physiologic osmolality and to aid in stabilizing the soluble collagen composition during storage. The polyol may also produce improved biocompatibility. Osmolality is preferably between 280 and 360 mmol/kg. In certain embodiments, the polyol is a sugar alcohol or other osmolality enhancer, and is preferably D-mannitol. In certain embodiments, the composition comprises the polyol in a concentration between 2.5% and 4%, or between 3.0% and 3.9%, or 3.5%.

Disaccharides, such as sucrose or fructose, may be included in the composition to aid in stabilization of the viscous collagen solution. In certain embodiments the disaccharides are added to a final concentration of between 50 mM to 500 mM, or 100 mM to 400 mM.

The composition is a neutralized pH solution that allows for injectable administration. In certain embodiments, the viscosity of the composition is suitable for injection through a fine gauge needle or cannula, such as a 27, 30 or 31 gauge needle or cannula. The low viscosity also allows for low extrusion forces. The composition can be injected through 27, 30 or 31 gauge needles with no significant difference in extrusion force. In addition to the ease of application, injectable delivery of the collagen solution allows access to the administration site while minimizing invasive injury to surrounding tissues.

Upon exposure to physiologic liquids, tissues, or other ion-containing fluid, the collagen solution polymerizes. Preferably, the composition undergoes rapid, nearly instant, gelation, followed by rapid fibrillogenesis to form a collagen fibril matrix. In certain embodiments, the composition initially polymerizes into a gel mass within 180 seconds after exposure to tissue, or within between 10 and 120 seconds or between 10 and 60 seconds after exposure to the tissue.

The composition forms a collagen fibril matrix rapidly after gelation. In certain embodiments, the collagen matrix is a white opaque mass comprising intact collagen fibrils. In certain embodiments, the composition forms a collagen fibril matrix within 10 minutes after exposure to the tissue, or within 5 minutes after exposure to the tissue.

The viscosity of the collagen solution is sufficient to fill a soft tissue defect or other specific delivery sites and remain in the desired tissue site until gelation and fibril formation occurs. Also, because of the rapid gelation and matrix formation, the volume of the formed collagen matrix is equivalent to the volume injected, making it convenient for practitioners to make a more precise determination of the appropriate volume to treat a dermal defect. This is an advantage over most hyaluronan injectable products that increase in volume after injection.

The present invention is also directed to a method for augmenting soft tissue or regenerating tissue. The method comprises injecting a neutralized acid-soluble collagen composition into a soft tissue deficiency, wherein the acid-soluble collagen polymerizes upon exposure to the tissue. Upon injection into tissue and contact with the tissue fluid, the composition undergoes rapid, nearly instant, gelation, which is followed by rapid fibrillogenesis to form a collagen fibril matrix. The collagen fibril matrix fills the soft tissue deficiency. As used herein, fill does not require that the deficiency be completely filled. However, completely filling the deficiency is also contemplated. In certain embodiments the composition comprises EDTA in concentrations described above. The composition may comprise polyols in the concentrations described above. In certain embodiments, the composition polymerizes and forms a collagen fibril matrix during the time periods discussed above.

The method of soft tissue augmentation can be used with a variety of soft tissue deficiencies. Soft tissue defects that can be treated with the method of the invention include wrinkles, dermal folds, dermal laxity, skin contour defects, dermal fine lines, dermal furrows and dermal unevenness. The composition can be injected into a variety of dermal areas. The method is particularly well suited to be injected into a soft tissue deficiency of lips or facial skin. The amount of the composition to be injected can be determined by one skilled in the art based on the soft tissue deficiency being treated. In many applications, volumes of 0.1-0.5 mL may be used.

The method of the present invention provides an in situ collagen matrix that is surprisingly durable. When used herein, a matrix remains durable if the collagen matrix does not degrade to a visually noticeable level. Durable in this context means the matrix remains intact and sufficiently maintains its injection volume to provide long-term clinical effectiveness. The method of the present invention can produce a collagen fibril matrix that remains durable for at least 4 weeks after said injection, at least 12 weeks and even 6 months or more. In certain embodiments, the collagen matrix produced by the method of the present injection integrates with the surrounding tissue, preferably by integrating with the matrices of the surrounding tissue.

The present invention is also directed to a method of injecting a collagen composition as described herein to promote or enhance soft tissue regeneration. The collagen matrix formed by the composition of the present invention provides a biological framework or matrix that supports and/or stimulates revascularization and cell population. This supports remodeling of the subject's own tissue.

The present invention is also directed to the use of a neutralized, acid soluble collagen solution as a biocompatible coating for medical implants and devices, as well as to the method for coating the implant or device. Certain embodiments are directed to a biocompatible polymeric or metallic medical implant or device, wherein the implant or device comprises a coating formed by a collagen composition described herein. In certain embodiments the device or implant is comprised of stainless steel. The coating may cover a portion or all of the implant or device. The coating comprises a neutralized solution comprising the acid soluble collagen, wherein the collagen is solidified on the surface of the implant or device. Although not wishing to be bound by any one theory, it is believed the collagen is fibrillized either through direct divalent ion exchange with the surface of the implant or device, or by drying on the surface of the implant or device. The composition may also comprise one or both of EDTA and polyols as described herein. In certain embodiments, the coating is stable on the implant for at least 30 days.

The invention is also directed to a method for applying an in situ polymerizing collagen solution disclosed herein to a medical implant or device. The solution can be applied by any means known in the art, including by dip coating or spray coating. After approximately 30 minutes, a thin, transparent coating forms on the material. The coating is strong and durable and hard to scrape off the implant or device. Application of such coatings is expected to add to biocompatibility, improve resistance to biodegradation, reduce delamination concerns, promote tissue adhesion, reduce rejection and potentially add anti-microbial properties to the polymer or metallic implants and devices. The coating may also fill small grooves in the implant or device and create an even and smooth coating.

The present invention provides a number of advantages over other collagen-based compositions for soft tissue augmentation. For example, the collagen compositions described herein are biocompatible, biodegradable, and stable in solution at neutral pH. The composition is characterized by in situ formulation of a collagen matrix, unlike other collagen-based compositions that polymerize before implantation. The present invention does not require use of crosslinking agents, additional fibrillar components, or synthetic polymers. The ability to chemically manipulate the collagen to form a neutral pH stable solution allows for injectable administration through a fine gauge needle. In addition to the ease of application, injectable delivery of the collagen solution allows access to the administration site while minimizing invasive injury to surrounding tissues. The viscosity of the collagen solution is sufficient to fill a soft tissue defect or other specific delivery sites and remain in the desired tissue site until gelation and fibril formation occurs. The volume of the formed collagen matrix is equivalent to the volume injected making it convenient for practitioners to make a more precise determination of the appropriate volume to treat a dermal defect. This is an advantage over most hyaluronan injectable products that increase in volume after injection. The addition of disodium EDTA provides anti-collagenase activity to inhibit tissue collagenases and other metalloproteinase to prolong the durability of the collagen implant and bactericidal activity to provide composition sterility and to prevent potential biofilm formation. The addition of D-mannitol, or similar sugar alcohols, brings the composition to physiologic osmolality and aids in stabilizing the composition before injection into tissues or application as a coating. In vivo studies in animal models have demonstrated maintenance of soft tissue augmentation for at least 6 months. Compositions aseptically prepared with disodium EDTA have generally been shown to be sterile. Contributions from di sodium EDTA may have contributed to the ability to provide sterile compositions. In addition, the composition has exhibited the ability to promote tissue regeneration without use of therapeutic agents, stem cells or other added growth stimulators.

Certain aspects of the present invention are illustrated by the following non-limiting examples.

Example 1

Preparation of In Situ Polymerizing Collagen Compositions by Dialysis Against a Single EDTA Solution Sequentially pH Adjusted The in situ polymerizing collagen compositions were prepared using methods based on those described by DeVore and Eiferman (U.S. Pat. No. 5,492,135). Pure, soluble, bovine Type I collagen was purchased from Advanced BioMatrix, Inc. Sodium chloride was added to the soluble, pepsin-digested collagen solution (3 mg/mL) to a concentration of 0.8M to precipitate collagen. The white, opaque precipitate was recovered by centrifugation for 30 minutes at 3500 RPM and concentrated to approximately 40 mg/mL by placement on filter paper to absorb excess liquid. The concentrated collagen precipitate was placed in dialysis tubing with a molecular weight cut-off of 100,000 daltons and dialyzed against 0.5M acetic acid for at least 16-18 hours and then 0.1M acetic acid for at least 16-18 hours. The resulting clear, viscous, redissolved collagen concentrate was then dialyzed against 0.035M (35 mM) EDTA (ethylenediaminetetraacetic acid, disodium salt dihydate, SigmaUltra ~99%). It was important to dialyze against disodium EDTA concentrations of at least 25 mM and preferably as high as 35 mM. Dialysis was continued for 5 days with daily adjustment of pH from the starting pH of 4.5 to a final pH of 7.5. The final clear and viscous collagen concentrate was collected and centrifuged to remove air bubbles. The final clear, viscous collagen exhibited a pH of 7.4 and did not undergo fibril formation at room temperature. Collagen fibrillogenesis was not triggered until the collagen was exposed to physiological liquids or liquids containing ions to trigger gelation and polymerizing reactions.

Evaluation of Gelation and Fibril Formation.

Figure 1A:
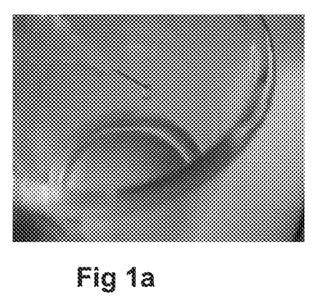
FIGS. 1a and 1b depict polymerization of the composition of one embodiment of the present invention in saline.
Figure 1B:
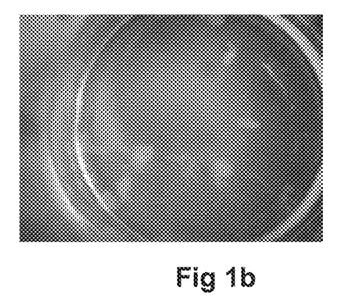

Aliquots of the in situ polymerizing collagen prepared as described above in this Example 1 were injected into 0.8M sodium chloride at 37° C., as depicted in FIG. 1a. Test samples were observed for the appearance of gel and fibrous collagen. As shown in FIG. 1b the clear viscous collagen solution formed a white, opaque collagen matrix in less than 60 seconds.

Example 2

Evaluation of a Human Skin Biopsy

Approximately 0.2 cc of in situ polymerizing collagen prepared as described in Example 1 was injected into the dermis of the hand. A biopsy was removed at 4 weeks and processed for H&E staining. Histological evaluations show exceptional biocompatibility with negligible inflammatory reactivity and clear integration by host fibroblasts.

Example 3

Evaluation of Injecting In Situ Polymerizing Collagen in Rat Tissues

Figure 2:
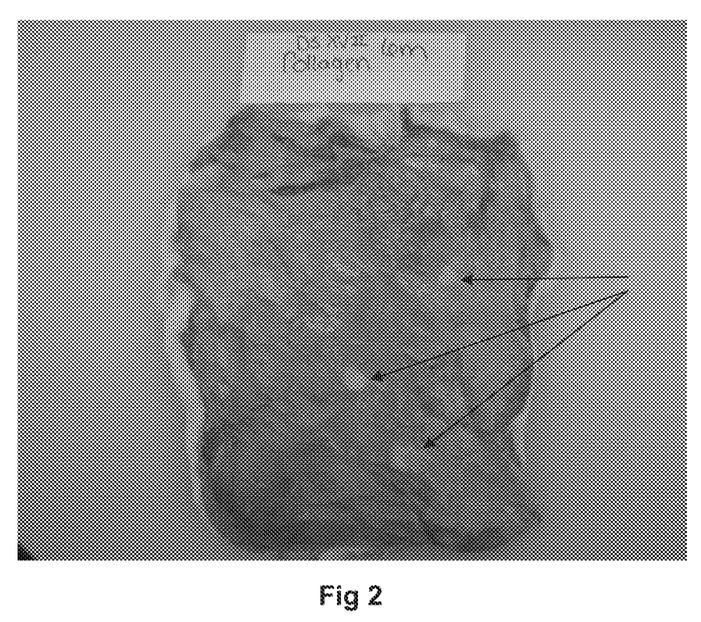
FIG. 2 depicts implants of the composition of one embodiment of the present invention in rat dermis at 6 months.
Figure 3:
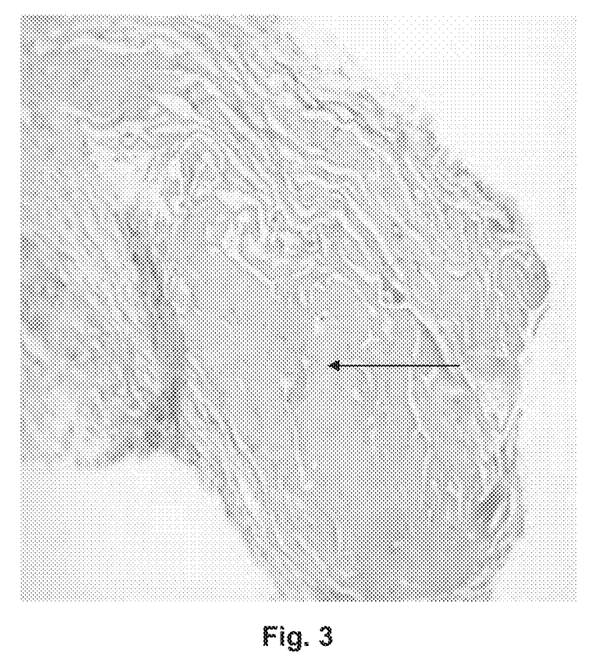
FIG. 3 depicts an implant of the composition of one embodiment of the present invention in rat dermis at 6 months.
Figure 4:
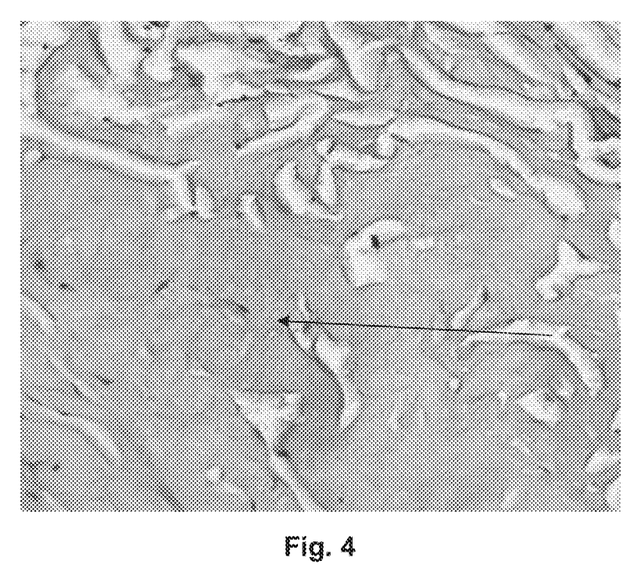
FIG. 4 depicts an implant of the composition of one embodiment of the present invention in rat dermis at 6 months.

Soluble, pepsin digested, bovine collagen was purchased from Advanced Biomatrix. In situ polymerizing collagen was prepared as described in Example 1 by extensive dialysis of salt precipitated, concentrated and acid treated collagen against 35 mM EDTA with step-wise increase in pH to 7.5. Collagen concentration was 37 mg/mL as assayed by hydroxyproline analysis. The rats were injected at 4 dermal sites with 0.4 cc each of in situ polymerizing collagen. Injection sites were examined for erythema and edema daily for 1 week, and then weekly for 6 months. The animals were terminated at 2 weeks, 1 month, 3 months, and 6 months. The rat skin was removed and implant sites examined macroscopically and photographed before dissection and preparation for histological assessment. Sections were stained with H&E and photomicrographs taken for evaluation. Evaluation of the underside of rat dermis clearly showed the opaque, collagen implant sites at each time period (FIG. 2). The collagen implant was clearly observed in H&E stained sections at each time period with little change in implant volume. Inflammatory cell reactivity was negligible to minimal and the implant itself was composed of an organized collagenous structure with fibroblastic cellular infiltrates (FIGS. 3 and 4).

Example 4

Preparation of In Situ Polymerizing Collagen Compositions by Dialysis Against Multiple, pH Adjusted EDTA Solutions Pure, soluble, porcine Type I collagen was purchased from SunMax Biotechnology, LTD. Saturated sodium chloride solution was added to the soluble, pepsin-digested collagen solution (3 mg/mL) to a concentration of 0.8M to precipitate collagen. The white, opaque precipitate was recovered by centrifugation for 15 minutes at 5000 RPM. The concentrated collagen precipitate was placed in dialysis tubing with a molecular weight cut off of 10,000 daltons, or in dialysis cassette with a molecular weight cut-off of 20,000 daltons, and dialyzed against 0.5M acetic acid for at least 16-18 hours and then 0.1M acetic acid for at least 16-18 hours. The resulting clear, viscous, redissolved collagen concentrate was then dialyzed against 0.035M (35 mM) EDTA (ethylenediaminetetraacetic acid, disodium salt dihydate, SigmaUltra ~99%). It was important to dialyze against disodium EDTA concentrations of at least 25 mM and preferably as high as 35 mM. The starting pH was 5.0±0.2. Dialysis was continued for at least 12 hours. The dialysis tubing or cassette was then transferred into a dialysis chamber containing 35 mM EDTA at a pH of 5.5±0.2 and dialyzed for at least 12 hours. The dialysis tubing or cassette was again transferred into a dialysis chamber containing 35 mM EDTA at a pH of 6.0 and dialyzed for at least 12 hours. Subsequent dialysis steps against 35 mM EDTA at pH 6.5 and 7.2 were conducted to bring the final collagen pH to approximately 7.0. The final clear, viscous collagen exhibited a pH of approximately 7.1 and did not undergo fibril formation at room temperature. Collagen fibrillogenesis was not triggered until the collagen was exposed to physiological liquids or liquids containing ions to trigger gelation and polymerizing reactions.

Example 5

Effects of D-Mannitol on Stability of In Situ Polymerizable Collagen

Collagen solutions prepared as described in Example 4 were subject to a final dialysis step against 35 mM EDTA containing 3.8% D-mannitol (346 mmol/kg). Stability (maintenance of clarity and transparency) of collagen solutions containing D-mannitol was compared to collagen solutions without D-mannitol by incubating solutions at 36° C. Stability was assessed by observing the visual appearance of the collagen solutions up to 225 minutes. Results demonstrated that D-mannitol significantly extended the stability of collagen solutions (at least 225 minutes) compared to controls (75 minutes).

Example 6

Improvement of Intracutaneous Irritation Scores with In Situ Polymerizable Collagen Containing D-Mannitol Intracutaneous irritation testing in rabbits based on ISO 10993-10 was conducted at NASMA. Test samples included in situ polymerizable collagen prepared as described in Examples 4 and 5, except that the process of Example 5 included a final dialysis step against 3.5% D-mannitol. A 0.1 ml dose of the test samples was injected intracutaneously in five separate sites in the backs of 3 animals for each composition. Additional positive control samples and negative controls were also tested. Injection sites were examined for erythema and edema immediately after injection and at 24, 48, and 72 hours after injection. Observations continued at 24 hour intervals for up to 7 days after injection. Test scores for in situ polymerizable collagen solution without D-mannitol were similar to the positive control sample. However, test scores of in situ polymerizable collagen with D-mannitol were lower than test scores without D-mannitol; 0.7 for compositions with D-mannitol compared to 1.4 for compositions without D-mannitol, based on the rating scale in the NASMA study protocol. These results were unexpected and indicate that addition of D-mannitol enhances the biocompatibility of the in situ polymerizable compositions.

Example 7

Effect of Sucrose on Stabilization of In Situ Polymerizing Collagen Solutions.

Collagen solutions prepared as described in Example 4 were subject to a final dialysis step against 35 mM EDTA containing 3.5% D-mannitol and 100 mM sucrose. This composition was compared to the collagen solution subject to final dialysis step against D-mannitol in Example 5. Solution stability (time that solutions remained clear and transparent) at 37° C. was assessed by observing the visual appearance of the collagen solutions. Solutions dialyzed against 3.5% D-mannitol and 100 mM sucrose exhibited a significant increase in stability compared to solutions dialyzed against D-mannitol alone. In one assay of stability, solutions dialyzed against 3.5% D-mannitol and 100 mM sucrose exhibited a 4-fold increase in stability compared to solutions dialyzed against D-mannitol. This observation suggests that long-term room temperature (20-25° C.) stability of the in situ polymerizable collagen will be significantly enhanced by inclusion of sucrose.

Example 8

Evaluation of In Situ Polymerizing Collagen in Rabbit Intradermal Tissue

Under general anesthesia, three Sprague-Dawley Rats were implanted with a sample of Monomer bovine collagen (RPC bovine) prepared according to methods described in Example 4 and one control article (Restylane) through deep intradermal injection. The injections were placed ~2 cm apart along the vertebral axis with three sites on each side (6 total including other test samples) per animal. Test and control articles were injected into the designated dosing locations at a volume of 0.15-0.25 mL per site.

Clinical observations and skin scoring (erythema and edema) were conducted immediately following injection and prior to termination, after which one designated animal was euthanized at 2, 5 and 8 weeks respectively. Daily observations were performed for the duration of the study. Following termination, the implant sites and draining lymph nodes (if identified) were collected, grossly evaluated for irritation and submitted for histopathology.

Overall, injection of in situ polymerizing collagen into the rabbit ear model resulted in minimal to mild irritation and inflammation. Tissue responses were equivalent to the tissue responses to the control.

Example 9

Evaluation of In Situ Polymerizing Collagen in Rabbit for Local Tissue Response.

In situ polymerizing porcine collagen solution prepared as described in Example 4 was injected in the subcutaneous tissue of the rabbit and the local tissue response was evaluated in accordance with ISO 10993 6, Biological evaluation of medical devices—Part 6: Tests for local effects after implantation.

The in situ polymerizing porcine collagen solution, a sponsor provided control article and a negative control article, along with location markers, were subcutaneously implanted and three animals (per interval) were euthanized at 4 weeks and 12 weeks. The subcutaneous tissues were excised and the implantation sites examined macroscopically. A microscopic evaluation of representative implantation sites from each animal was conducted to further define any tissue response.

The macroscopic reaction was not significant as compared to the sponsor provided control and negative control articles at 4 and 12 weeks. Microscopically, the test article remained intact and was classified as a nonirritant as compared to the sponsor provided control and negative control articles at 4 and 12 weeks. Additional microscopic analysis of test specimens demonstrated maintenance of volume from 4 to 12 weeks and integration with surrounding tissues.

The clinical observations and histological results presented in Examples 2, 3, 6, 8, and 9 demonstrated the exceptional biocompatibility and in vivo durability of the novel in situ polymerizing collagen in situ polymerizing collagen composition. Durability at 6-months shown in Example 3 exceeds that clinically reported for most injectable, collagen-based compositions for soft tissue augmentation.

Example 10

Transmission Electron Microscopy of Polymerized In Situ Polymerizing Collagen

Figure 5:
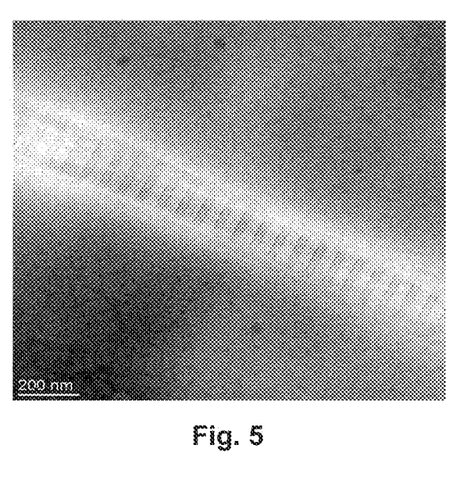
FIG. 5 depicts a TEM photomicrograph of a collagen fibril of one embodiment of the present invention.

Polymerization Protocol: Approx. 0.1 mL in situ polymerizing collagen prepared as in Example 4 was added to 1 mL of 2× phosphate buffered saline at pH 7.2 at 35 C in a microcentrifuge tube. After 8-10 minutes, polymerized collagen samples were pipetted (a drop) onto a mini-grid (~2 mm in diameter) at the TEM prep lab. Then the excess was wicked off to create a thin film. A contrast agent was added for TEM analysis. TEM photomicrographs showed well banded intact collagen fibrils (FIG. 5).

Example 11

Demonstration of Anti-Collagenase Activity.

This study was conducted to determine collagenase inhibition of in situ polymerizable collagen compositions. Pure collagen fibrils served as a control article and the test collagen solution prepared as described in Example 4 was polymerized before testing to mimic a similar condition in vivo. Hydroxyproline assays were performed before collagenase degradation in order to ensure that the same amount of collagen was used in the study. A hydroxyproline assay was performed after the collagenase degradation to measure the collagen residue after reaction.

Results showed that the test collagen containing 35 mM EDTA was approximately 35% more resistant to collagenase digestion compared to a standard collagen sample.

Example 12

Demonstration of Bactericidal Activity

This study was conducted to evaluate bactericidal activity of in situ polymerizable collagen compositions. Two test samples of in situ polymerizable collagen, Lot 0022, prepared as described in Example 4, were exposed to *Staphylococcus aureus*. The test samples were polymerized to form a scaffold before testing to mimic a similar condition in vivo. Antimicrobial effects were evaluated by SEM imaging. Samples were exposed to the bacteria solution (~100 CFU/mL) for 2 days. Collagen scaffolds were removed from bacteria solutions, rinsed in 1× phosphate buffered saline and treated with a fixative solution (2% paraformaldehyde and 2% glutaraldehyde in 0.1M cacodylate buffer) and rinsed with pure water before imaging. SEM photomicrographs clearly demonstrated absence of bacteria colonies.

Example 13

Use of In Situ Polymerizing Collagen Solution as a Coating

Five different materials were coated with in situ polymerizing collagen solution.
1. Stainless steel plates (smooth and surface roughened using 50 and 220 grit sandpaper)
2. Titanium bone screw
3. Polypropylene suture (Prolene)
4. Polypropylene mesh (lightweight, Bard)
5. PEEK (polyether ether ketone) bone screw (Smith and Nephew)

The viscous, soluble collagen resulted in a thick coating on all the materials. The samples were placed in petri dishes to polymerize and dry. Upon drying the coatings were very thin, transparent, and very difficult to see on some of the material specimens.

The films were characterized using at least one of the following methods:
1. Brightfield microscopy—A Nikon inverted microscope was utilized to capture the transparent coating of the RPC. The microscopy images provided measurements of coating thicknesses.
2. Scanning Electron Microscopy (SEM)—SEM (secondary electron) imaging was utilized to investigate the integrity and quality of the coatings.
3. FTIR Spectroscopy—Before and after scans were acquired of the polymer materials to determine the presence of the collagen coating.
4. Drop Shape Analyzer—The surface energy of the metallic plates were determined before and after coating in order to determine changes in contact angle/surface energy.
5. Stability Testing—After polymerization of the coatings, the coated materials were then placed in PBS and incubated for 30 days at 37° C. to determine the stability of the coating. After 30 days, the materials were removed and brightfield microscopy was performed in order to determine coating stability and thickness.

Results showed the presence of a smooth, conforming collagen coating on polymer sutures and polymer meshes. Similarly, polished stainless steel plates were effectively coated with the in situ polymerizing collagen solution. Overall, the in situ polymerizing collagen composition polymerized and adhered to both metallic and polymeric materials and was stable after 30 days exposure to phosphate buffered saline at 37°.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A method for augmenting soft tissue, comprising,
    injecting into a soft tissue deficiency a neutralized solution comprising EDTA and an acid soluble collagen selected from the group consisting of Type 1 collagen, Type III collagen and combinations thereof,
        wherein the collagen in the solution has not undergone fibrillogenesis prior to injection;
        wherein the EDTA concentration in the solution is from 25 mM to 40 mM, and
        wherein the collagen has been dialyzed against EDTA;
    wherein said soft tissue deficiency is selected from the group consisting of wrinkles, dermal folds, dermal laxity, skin contour defects, dermal fine lines, dermal furrows and dermal unevenness;
    wherein said acid soluble collagen undergoes fibrillogenesis upon exposure to the soft tissue to form an opaque collagen fibril matrix; and wherein the collagen fibril matrix augments the soft tissue deficiency.

2. The method of claim 1, wherein said injection is into the soft tissue deficiency in lips or facial skin.

3. The method of claim 1, wherein the tissue and the matrix remains durable for at least 4 weeks after said injection.

4. The method of claim 3, wherein said matrix remains durable for at least 12 weeks after said injection.

5. The method of claim 4, wherein said matrix remains durable for at least 6 months.

6. The method of claim 1, wherein said injected composition produces regeneration of the tissue.

7. The method of claim 1, wherein said injected composition integrates with matrices of the tissue.

8. The method of claim 1, wherein said composition comprises said acid soluble collagen in a concentration between 5 and 70 mg/ml.

9. The method of claim 8, wherein the concentration of said acid soluble collagen in said composition is between 25 and 65 mg/ml.

10. The method of claim 9, wherein the concentration of said acid soluble collagen in said composition is between 20 and 40 mg/ml.

11. The method of claim 1, wherein said composition further comprises a polyol and said polyol is a sugar alcohol.

12. The method of claim 11, wherein said polyol is D-mannitol.

13. The method of claim 11, wherein the composition comprises said polyol in a concentration between 2.5% and 4% (w/v).

14. The method of claim 13, wherein the concentration of said polyol in the composition is between 3.0% and 3.9% (w/v).

15. The method of claim 1, wherein the composition further comprises a disaccharide, fructose, or combinations thereof.

16. The method of claim 1, wherein the composition further comprises fructose, sucrose, or combinations thereof.

* * * * *